United States Patent [19]

Santi

[11] 4,280,183

[45] Jul. 21, 1981

[54] GAS ANALYZER

[75] Inventor: Giunio G. Santi, Milan, Italy

[73] Assignee: S.S.O.S. Sub Sea Oil Services S.p.A., Milan, Italy

[21] Appl. No.: 62,066

[22] Filed: Jul. 30, 1979

[30] Foreign Application Priority Data

Aug. 4, 1978 [IT] Italy .............................. 26473 A/78
Feb. 9, 1979 [IT] Italy .............................. 20059 A/79

[51] Int. Cl.³ .......................................... G01N 29/02
[52] U.S. Cl. ...................................... 364/497; 73/24; 73/645; 364/565
[58] Field of Search .............. 364/497, 498, 421, 422, 364/565; 73/645, 597, 24

[56] References Cited

U.S. PATENT DOCUMENTS

| 3,431,778 | 3/1969 | Lemon et al. | 364/565 X |
| 3,504,164 | 3/1970 | Farrell et al. | 364/417 X |
| 3,975,674 | 8/1976 | McEuen | 364/421 X |
| 3,991,398 | 11/1976 | Andermo et al. | 364/565 X |
| 3,993,903 | 11/1976 | Neuman | 364/422 X |
| 4,094,608 | 6/1978 | Young | 73/24 X |
| 4,118,782 | 10/1978 | Allen et al. | 364/565 |
| 4,121,290 | 10/1978 | Allen et al. | 364/565 |
| 4,143,547 | 3/1979 | Balser | 364/565 X |
| 4,155,246 | 5/1979 | Dempster et al. | 73/24 |

Primary Examiner—Edward J. Wise
Attorney, Agent, or Firm—Darbo & Vandenburgh

[57] ABSTRACT

A gas analyzer for instantaneously testing the percentages of the components of a binary gas mixture comprising carbon dioxide and oxygen, or a ternary one also containing saturated steam, which is intended more particularly for the supply of fuel to an engine for submarine operation, said analyzer including a temperature test apparatus to test the temperature T of the gas mixture, a sound velocity test apparatus, comprising an ultrasonic generator receiver and phase comparator to test the sound transmission velocity V in the gas mixture and a calculator to calculate the value of the ratio $V^2/T$ or a value proportional thereto.

7 Claims, 1 Drawing Figure

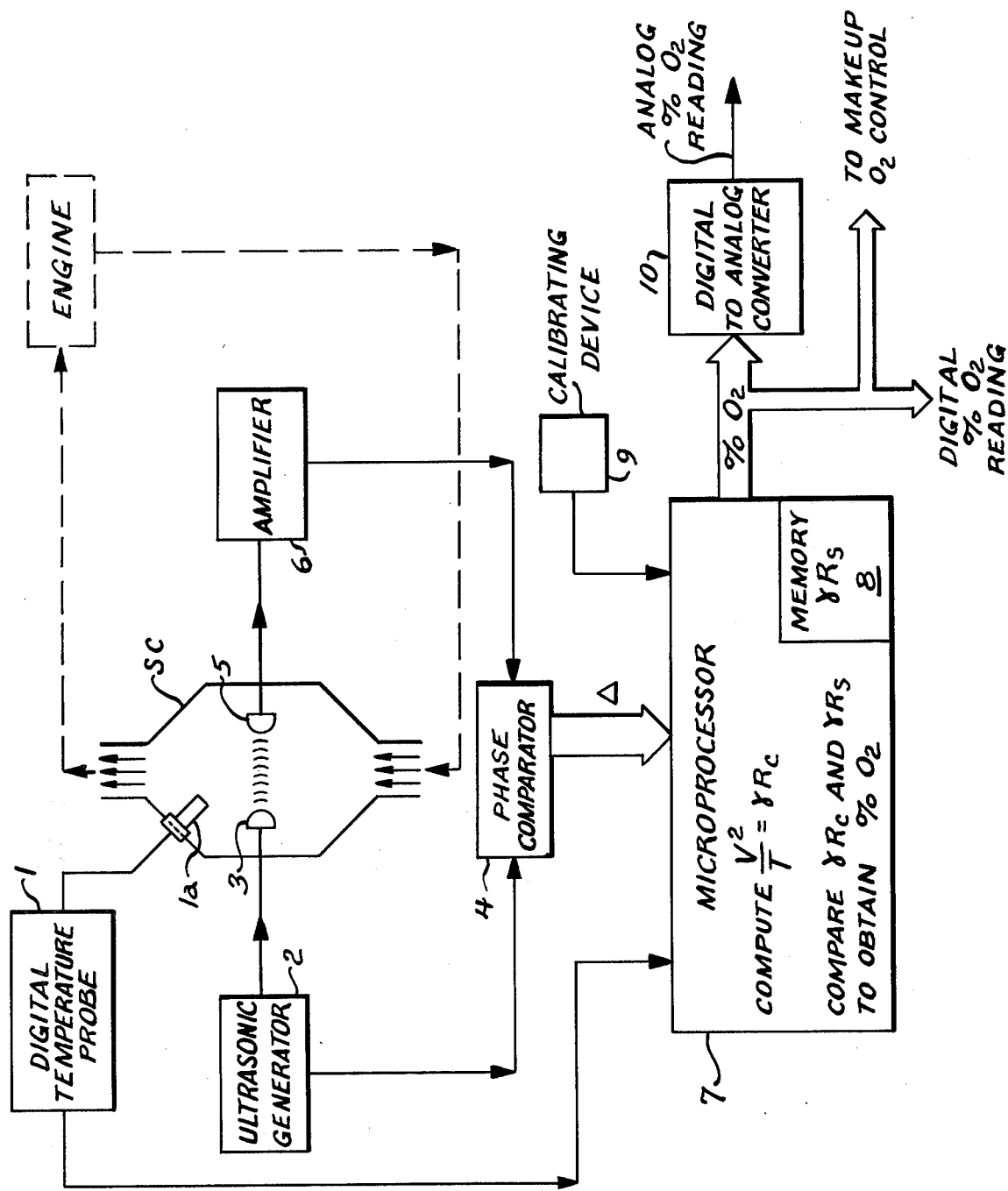

GAS ANALYZER

BACKGROUND AND SUMMARY OF THE INVENTION

This invention relates to gas analyzers and more particularly concerns a gas analyzer for the instantaneous testing of the percentages of the components of a ternary gas mixture comprising carbon dioxide, oxygen and saturated steam, which is intended more particularly for the fuel supply to an engine for submarine operation.

It is necessary to determine the percentages of the two gas components needed in a ternary gas mixture saturated with steam even when the pressure and the temperature may fluctuate within significantly wide ranges and more particularly when the values of the percentages are required to be determined in as short a period of time as possible compared to the variations of these percentages occurring. One specific situation is to test the percentages of carbon dioxide and oxygen in the intake mixture of an internal-combustion engine with exhaust gas recirculation employed in submarine operation. The knowledge of these percentages is indispensible in order that the stream of oxygen to be introduced into the circuit of the internal-combustion engine can be regulated in such a way that the percentage of the oxygen in the gas mixture assumes its optimum value.

Currently available conventional gas analyzers do not present these possibilities, for the following reasons:

the value of the percentage to be tested cannot be determined instantaneously, on the contrary a time of some ten seconds required for that purpose cannot be further reduced;

the information as to the value of the percentage of the one component of the gas mixture stands in close relationship to the value of the instantaneous pressure and this value must therefore be known with sufficient precision, otherwise the second information, i.e., the value of the percentage of the second gas, must be determined separately, which means that for this second possibility two gas analyzers must be available, which obviously requires more complicated apparatus and reduced reliability;

trouble-free operation of the conventional gas analyzers depends upon the temperature level of the gas mixture, and at temperatures which exceed a certain limit, the information obtainable in practice contains considerable errors; and sufficiently pure gases must be present.

An object of the present invention is to overcome the above-mentioned difficulties by approaching the problem on the basis of an entirely different principle.

According to the present invention I provide a gas analyzer for instantaneously testing the percentages of the components of a binary gas mixture comprising carbon dioxide and oxygen, or a ternary one additionally containing saturated steam, which analyzer is intended more particularly for the supply of fuel to an engine for submarine operation, said analyzer including a temperature test apparatus to test the temperature T of the gas mixture, a sound velocity test apparatus to test the sound transmission velocity V in the gas mixture and a calculator to calculate the value of the ratio $V^2/T$ or a value proportional thereto.

The solution achieved by the present invention is based upon the principle that the sound transmission velocity in a continuous gaseous medium is a function of the characteristics of the gas and of the temperature in accordance with the known relation.

$$V = \sqrt{\gamma R T}$$

wherein $V$ = sound transmission velocity in the gas mixture [m. sec$^{-1}$], $\gamma$ = ratio $c_p/c_v$ of the specific heat at constant pressure to the specific heat at constant volume of the gas mixture, $R$ = characteristic constant of the gas mixture [m$^2$.sec$^{-2}$.°K.$^{-1}$], $T$ = absolute temperature of the gas mixture [°K.].

From the temperature of the gas mixture and from the sound transmission velocity it is possible to derive the value of the quantity $$\gamma R = V^2/T$$

which is a function of the parameters of the gas mixture, i.e., of the percentages of the components which exhibit known physical and thermodynamic properties. The values of these percentages are therefore immediately and simultaneously determinable.

In the case of the gas mixture with two components (carbon dioxide and oxygen) the relation $$\gamma R = \gamma_1 R_1 p_1 + \gamma_2 R_2 p_2,$$

applies wherein the indices 1 and 2 refer to the first and second gas respectively and $p_1$ and $p_2$ represent the percentage by weight of the first and of the second gas respectively.

The case of the ternary gas mixture which additionally contains saturated steam with the weight percentage $p_3$, to which the relation $$\gamma R = \gamma_1 R_1 p_1 + \gamma_2 R_2 p_2 + \gamma_3 R_3 p_3$$

applies can be reduced in a simple way to the previous case because the temperature value permits the determination of the water content present in the gas mixture and hence in turn the values of the percentages of the two other components can be determined from the temperature and from the sound transmission velocity.

The precision of the data which can be supplied by the gas analyzer according to the invention stands in a close and exclusive relationship to the precision of the tested temperature and of the tested sound transmission velocity. These two test quantities can be measured in a reliable and precise manner, more importantly without appreciable loss of time, with the aid of apparatus available according to the current state of the art.

In order to emphasize the most significant achievements of the gas analyzer according to the invention, particular mention will be made of its advantages given hereinbelow:

the gas analyzer according to the invention operates at any desirable pressure while moreover the test result is independent of the actual pressure;

it operates at any desired temperature provided that the value of the temperature itself is known;

it delivers an extremely rapid and precise read-out of the percentage to be determined;

with the mere information as to the percentage oxygen content, it also gives the second information (on the percentage content of carbon dioxide) simultaneously by forming the difference; and it operates trouble-free even in the case of incompletely pure gases, as is the case with the exhaust gas of an internal-combustion engine.

In the gas analyzer according to the invention, the test apparatus for testing the temperature is preferably a digital temperature probe.

In a preferred embodiment of the invention, the test apparatus for testing the sound transmission velocity in the gas mixture is an ultrasonic transmitter and an ultrasonic receiver. With such apparatus it is convenient that the ultrasonic transmitter constitutes a generator to generate an electrical alternating quantity of ultrasonic frequency and an electro-acoustic transducer, that the ultrasonic receiver constitutes an acoustico-electric transducer preferably with a following amplifier and exhibits a constant interval with reference to the electro-acoustic transducer, and that a phase comparator compares the phase of the signals delivered by the generator to generate the electric alternating quantity of ultrasonic frequency with the phase of the signals received by the acoustico-electric transducer.

The calculator to calculate the value of the ratio $V^2/T$ or of a value proportional thereto is advantageously constituted by a microprocessor, the input data of which are constituted by the output signal of the thermometer and the output signal of the phase comparator.

DESCRIPTION OF THE DRAWING

The drawing is a simplified block circuit diagram of one embodiment of the invention.

DESCRIPTION OF SPECIFIC EMBODIMENT

The following disclosure is offered for public dissemination in return for the grant of a patent. Although it is detailed to ensure adequacy and aid understanding, this is not intended to prejudice that purpose of a patent which is to cover each new inventive concept therein no matter how others may later disguise it by variations in form or additions or further improvements.

A digital temperature probe 1 having a sensor 1a is provided which serves to test the temperature T of a gas mixture consisting essentially of carbon dioxide and oxygen saturated with steam. Such gas mixture is used as the principal gas for the supply of fuel through a supply conduit SC to a diesel engine with exhaust gas recirculation for exclusive submarine operation, not shown in detail in the drawing. The flow direction through the supply conduit of the gas mixture to be analyzed is indicated by arrows. An electric generator 2 which generates an alternating voltage of ultrasonic frequency, e.g., at 40 kHz, is connected on the one hand to an electro-acoustic transducer 3 and on the other hand to the one input of a phase comparator 4. The ultrasonic waves emitted by the electro-acoustic transducer 3 are received by an acoustico-electric transducer 5 which transforms them back into an electric alternating voltage. The latter is fed to the input of an amplifier 6, the output of which communicates with the second input of the phase comparator 4. The phase comparator 4 therefore compares the phase of the signals delivered by the generator 2 with the phase of the signals received by the acoustic-electric transducer 5 and hence, since the transducers 3 and 5 are constant distance apart, the signal at the output of the phase comparator 4 is directly proportional to the velocity V with which the ultrasonic waves traverse the gas mixture to be analyzed.

The output signal of the digital temperature probe 1 and the output signal of the phase comparator 4 constitute the essential input data for a microprocessor 7. In the present exemplary embodiment the value of the quantity $\gamma R$ has been calculated beforehand for a discrete series of percentage values of the oxygen content and of temperature values. These previously calculated values $\gamma R_s$ are stored in a memory 8. The microprocessor 7 calculates the respective ratio $V^2/T = \gamma R_c$, compares its value with the data contained in the memory 8 and delivers as a result of this comparison a digital output signal which directly indicates the percentage oxygen content (e.g., $\gamma R_c / \gamma R_s = \% \ O_2$).

The digital output signal of the microprocessor 7 constitutes the input information for a makeup $O_2$ control, not shown, which has the function to determine the quantity of oxygen to be supplied additionally to the gas mixture in order that the optimum composition of the gas mixture in the intake conduit is obtained.

The same digital output signal of the microprocessor 7 permits a direct reading of the percentage oxygen content and can if required be transformed into a corresponding analog signal with the aid of a digital-analog converter 10.

A calibrating device 9 provides the possibility to feed to the microprocessor 7 an additional calibration input which permits a tuning of the gas analyzer according to the invention as a function of the real constant interval between the two transducers 3 and 5.

I claim:

1. A gas analyzer, particularly useful in connection with the supply of fuel to an engine of a submarine, which engine has a fuel supply conduit through which flows an atmosphere comprising primarily oxygen gas and carbon dioxide gas, with or without satured steam, said analyzer immediately providing a signal indicative of the percent of that atmosphere made up by one of said gases, said analyzer comprising:

temperature test means, including a sensor in said conduit, for providing a signal T indicative of the temperature of said atmosphere;

sound velocity test means, having a portion thereof in said conduit, for providing a signal V indicative of the sound transmission velocity in said atmosphere; and means connected to said test means to receive said signals therefrom, to calculate the value of the ratio $V^2/T$ and to produce therefrom a signal indicative of the percentage of said one gas in said atmosphere.

2. A gas analyzer according to claim 1, wherein said one gas is oxygen, and the last mentioned means includes a memory for storing a discrete series of percentage value of oxygen content and the ratio of $V^2/T$ for each, said last mentioned means comparing said calculated ratio with said stored ratios to produce said percentage signal.

3. A gas analyzer according to claim 1 in which the temperature test means is a digital temperature probe.

4. A gas analyzer according to claim 1 or 2 in which the sound velocity test means comprises an ultrasonic transmitter.

5. A gas analyzer according to claim 4 in which the ultrasonic transmitter comprises a generator to generate an alternating electric current of ultrasonic frequency and said portion comprises electro-acoustic transducer connected to said generator and an acoustico-electric transducer to produce said signal V, said transducers being a fixed distance apart in said conduit.

6. A gas analyzer according to claim 5 wherein said sound velocity test means includes a phase comparator connected to said generator and said acoustico-electric transducer to produce said V signal by comparing the phase of the signals of the generator with the phase of the signals received by the acoustico-electric transducer.

7. A gas analyzer according to claim 6 in which the means connected to the test means is a microprocessor, and including a calibrating device by which there is fed to the microprocessor an additional calibration input which permits a tuning of the gas analyzer as a function of the real constant interval between the two transducers.

* * * * *